(12) United States Patent
Moest et al.

(10) Patent No.: US 8,999,394 B2
(45) Date of Patent: Apr. 7, 2015

(54) PANCREATINE PELLETS AND METHOD OF PRODUCING SAME

(76) Inventors: Thomas Moest, Moorrege (DE); Manfred Kurfürst, Moorrege (DE); Walter Doleschal, Uetersen (DE)

( * ) Notice: Subject to any disclaimer, the term of this patent is extended or adjusted under 35 U.S.C. 154(b) by 0 days.

(21) Appl. No.: 12/806,942

(22) Filed: Aug. 24, 2010

(65) Prior Publication Data

US 2011/0052706 A1    Mar. 3, 2011

(30) Foreign Application Priority Data

Aug. 28, 2009 (DE) .................... 20 2009 011 699 U
Jan. 12, 2010 (EP) .................................... 10150491

(51) Int. Cl.
| | |
|---|---|
| A61K 9/16 | (2006.01) |
| C12N 9/94 | (2006.01) |
| A61K 9/14 | (2006.01) |
| A61K 9/50 | (2006.01) |
| A61K 38/46 | (2006.01) |
| A61K 38/47 | (2006.01) |
| A61K 38/48 | (2006.01) |

(52) U.S. Cl.
CPC ................ A61K 9/14 (2013.01); A61K 9/5031 (2013.01); A61K 9/5047 (2013.01); A61K 9/5073 (2013.01); A61K 38/465 (2013.01); A61K 38/47 (2013.01); A61K 38/48 (2013.01); A61K 9/5089 (2013.01)

(58) Field of Classification Search
CPC ............................. A61K 35/39; C12N 5/0676
See application file for complete search history.

(56) References Cited

U.S. PATENT DOCUMENTS

| | | | |
|---|---|---|---|
| 2,189,948 | A | 2/1940 | Griffith |
| 4,280,971 | A | 7/1981 | Wischniewski |
| 5,378,462 | A | 1/1995 | Boedecker |
| 6,270,723 | B1 | 8/2001 | Laugharn |
| 2005/0250817 | A1 | 11/2005 | Shlieout |
| 2007/0148152 | A1 * | 6/2007 | Shlieout et al. .............. 424/94.3 |
| 2011/0052706 | A1 | 3/2011 | Moest |
| 2011/0268844 | A1 | 11/2011 | Ramsch |
| 2011/0293590 | A1 | 12/2011 | Ramsch et al. |
| 2012/0213857 | A1 | 8/2012 | Moest |

FOREIGN PATENT DOCUMENTS

| | | |
|---|---|---|
| EP | 0 436 110 | 7/1921 |
| EP | 0 436 110 A1 * | 7/1991 |
| EP | 0436110 | 7/1991 |
| JP | 3-172181 | 7/1991 |
| JP | 11-315032 | 11/1999 |
| SU | 271472 | 10/1971 |
| TW | 310227 A | 8/1982 |
| WO | WO 2006/044529 A1 | 4/2006 |
| WO | WO 2008/127567 A1 | 10/2008 |
| WO | PCT/EP2009/006216 | 8/2009 |
| WO | PCT/EP2009/000566 | 12/2011 |

OTHER PUBLICATIONS

EPO Search Report issued Jul. 29, 2010 in corresponding European application 10150491 (4 pages) (in German language).
English translation of EPO Search Report issued Jul. 29, 2010 in corresponding European application 10150491 (6 pages).
USPTO Office Action, mailed Jul. 10, 2013, issued in U.S. patent publication No. US 2011/0268844.
Japanese Office Action in parallel Japanese application 2010-115584, mailed Aug. 20, 2013 (4 pages)—and partial English translation.
USPTO Office Action, mailed May 7, 2014, issued in U.S. patent publication No. US 2011/0268844.
"Engineering Toolbox", www.engineeringtoolbox.com website (Aug. 22, 2014), 2 pages.
Material Safety Data Sheet—Pancreatin: Columbus Chemical Industries, Inc. (Nov. 11, 2005), 2 pages.
USPTO Office Action, mailed Nov. 27, 2012, issued in U.S. patent publication No. US 2011/0268844.
USPTO Office Action, mailed Mar. 14, 2013, issued in U.S. patent publication No. US 2012/0213857.

* cited by examiner

*Primary Examiner* — Dennis J Parad
(74) *Attorney, Agent, or Firm* — Nash and Titus, LLC

(57) ABSTRACT

In order to prevent impairment of the pharmacological effect of pancreatine through added auxiliary substances or binding agents a pancreatine pellet consists exclusively of pancreatine.

6 Claims, 2 Drawing Sheets

PANCREATINE PELLETS AND METHOD OF PRODUCING SAME

This application claims priority from Germany application no. DE 20 2009 011 699.9, filed on 28 Aug. 2009, and European application no. EP 10150491, filed Jan. 12, 2010, and the contents of these documents are incorporated in their entirety by reference.

FIELD OF THE INVENTION

The invention relates to pancreatine pellets, more particularly pancreatine micropellets, and methods of producing them.

Pancreatine is the extracted mixture of enzymes from the pancreas essentially consisting of lipases, amylase and proteases. The starting material for the production of pancreatine is mainly fresh or frozen pig's pancreas, from which only the water and fat have been originally removed to produce the pancreatine. However, taking into account the sensitivity of the enzymes, methods have been developed which should allow the pancreatine to be obtained in as gentle way as possible. One suitable method is described in DE 32 48 588 A1.

As an active substance, pancreatine is used in particular for the treatment of digestive disorders caused by pancreatine deficiency. Pancreatine is mainly taken in dried form as an oral medicinal product, whereby it has been shown that the therapeutic efficacy of pancreatine administration can be improved if the active substance is taken in the form of pellets or micropellets.

Typically pancreatine pellets are produced by adding auxiliary substances and binding agents to the pancreatine and mixing these components until a homogeneous mixture is obtained. This homogeneous mixture is then introduced into an extruder where the mixture is made into a strand-like extrudate. This extrudated product is finally introduced into a spheroniser where the strands are destroyed and form spherical pellets. The pellets are then dried and sieved whereby sieving fractions with pellets above or below a defined size are separated out. The thus obtained pellets, which have a narrow size distribution, can then be covered with a coating of material which is resistant to gastric juices.

Such a method of producing pancreatine micropellets is described in EP 0 583 726 A2 for example. In accordance with this method, before extrusion 100 parts of pancreatine are mixed with 15 to 50 parts by weight of polyethylene glycol 4000 and 10 to 30 parts by weight of an alcohol. The alcohol, for example, propanol, is intended to give the mixture an extrudable form. The strands obtained by way of extrusion are mixed with 1.5 to 5 parts by weight of paraffin before being transferred into the spheroniser and a further 1.5 to 10 parts by weight of alcohol are added. The obtained pellets have a pancreatine content of 65 to 85% by weight, so that the pellets contain at least 15% by weight of auxiliary substances and binding agents.

However, the auxiliary substances and binding agents required for extrusion can have undesirable effects. For this reason the selection of auxiliary substances and bindings agents is subject to constant monitoring. For example, it has been found that the hitherto usual addition of mineral oils can no longer be considered as uncritical.

On these grounds a method was proposed in EP 1 931 317 B1 with which is should be possible to produce pancreatine pellets without the addition of paraffin. The pancreatine pellets there contain 10 to 95% by weight of pancreatine, with at least 5% by weight of auxiliary substances and binding agents such as polyethylene glycol.

However, it can be anticipated that substantiated and unsubstantiated concerns can be raised against additives of any kind. It is therefore desirable to provide a pancreatine in a form that on the one hand can be taken orally and on the other hand is as free as possible of any additives.

SUMMARY OF THE INVENTION

The aim of the invention is eliminate the drawbacks in accordance with the state of the art. More particularly pancreatine pellets are to be provided which have improved characteristics, whereby in order to avoid impairment through added auxiliary substances or binding agents, the pellets should contain pancreatine in the most active possible form without additives or binding agents or other auxiliary substances and the oral administration of the pellets should be made easier. Furthermore, a pharmaceutical composition containing the pancreatine pellets in accordance with the invention as well as an application for the pancreatine pellets are to be set out.

DETAILED DESCRIPTION

Figure 1:
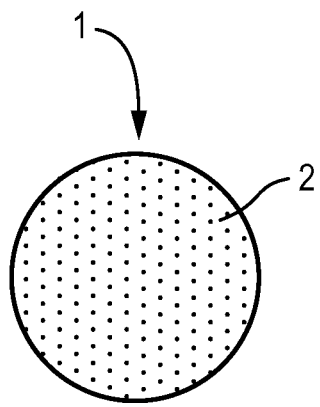
FIG. 1 shows a cross-section view of a first example of embodiment of a pancreatine pellet in accordance with the invention which is exclusively formed of pancreatine.
Figure 2:
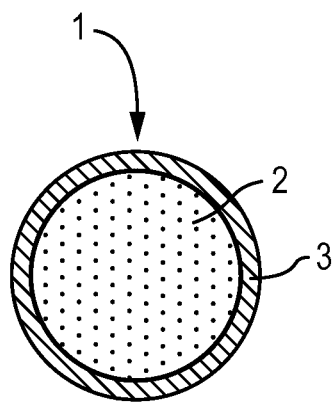
FIG. 2 shows a cross-section view of a second form of embodiment of a pancreatine pellet in accordance with the invention with a pancreatine core and a single-layer coating.

According to the invention a pancreatine pellet is envisaged that is exclusively formed of pancreatine. The pancreatine pellet according to the invention therefore consists of 100% pancreatine and contains no auxiliary substances or binding agents.

The pancreatine pellets according to the invention offer the advantage that impairment of the pharmacological effect of the pancreatine due to the addition of auxiliary substances or binding agents or both can be avoided.

In the present invention the term pellet is taken to mean a body with a spherical, elliptical or drop-like shape, whereby the sphere diameter or the shorter axis lies in the range 0.4 mm to 2.5 mm.

In one form of embodiment of the invention the pancreatine pellet is a micropellet. In the present invention the term micropellet is taken to mean a body with a spherical, elliptical or drop shape, whereby the sphere diameter or the shorter axis lies in the range 0.4 to 0.8 mm.

The pancreatine has preferably been obtained from the pancreas of a mammal, preferably from pigs or cattle. The production of the pellets is integrated into the process of obtaining the pancreatine. The addition of a separate auxiliary product in order to produce a plastic mass, as required in accordance with the state of the art for pelleting using an extruder, is not therefore necessary.

The pellets are thus obtained by way of the following procedure: the pancreases originating from pigs or cattle are initially comminuted and undergo autolysis. Through filtering the thus obtained intermediate product the sieved filtrate is obtained. The enzymes contained in the sieved filtrate are precipitated out, the mixture is filtered and a filter cake obtained. The filter cake is finally ground and vacuum-dried until it has residual moisture amounting to 0.1 to 0.3% by weight. The described pancreatine product with 0.3% residual moisture is the dried end product, whereas the extrudable filter cake mass contains more residual moisture/ organic solvent residue which is of the order of 50%. The filter cake then undergoes thermal treatment at 80° C. or less. Surprisingly the filter cake can be extruded and spheronised directly without further additives and/or binding agents. The obtained pellets are then dried. The thermally treated filter cake exhibits sufficient plasticity for extrusion in order to form strands of the filter cake. After extrusion spheronisation can be carried out, also without the addition of additives and/or binding agents or other auxiliary substances, as has been demonstrated by the experiments carried out by the applicant. In these, spherical, elliptical or drop-shaped pellets are obtained, which can be used as they are or as cores which are to be covered with a coating.

According to the invention, a pancreatine pellet is also envisaged that has a core and a coating, whereby the core is completely constituted of pancreatine. The core thus comprises 100% pancreatine and contains no auxiliary substances or binding agents. On the other hand the coating can consist of at least one auxiliary substance and/or at least one binding agent.

In another form of embodiment the coating consists of a first, inner layer, which surrounds the core of pancreatine, and a second outer layer. Preferably the first layer is made of at least one auxiliary substance and/or at least one binding agent, preferably of a material that is resistant to gastric juices.

The proportion by weight of auxiliary substances and bindings agents in the pancreatine pellet should be between 5 and 30% by weight. The proportion by weight of gastric juice-resistant material in the pancreatine pellets should be between 10 and 30% by weight.

The auxiliary substances and binding agents surrounding the pancreatine core ensure the cohesion of the core, for example during storage and transportation of the pellets and thereby prevent any mechanical or chemical destruction of the core. The auxiliary substances and binding agents used must be pharmacologically tolerable.

Suitable pharmacologically tolerable auxiliary substances which could constitute the coating or the inner layer of the coating, possibly in conjunction with the binding agents described below, include, for example fillers, humectant agents, lubricants, disintegration agents and colorants. This list is not exhaustive, indeed other auxiliary substances known to a person skilled in the art can also be used.

Examples of suitable filling agents are selected from the group which contains calcium phosphate, microcrystalline cellulose, dextrane, dextrin, precipitated calcium carbonate, hydratised silicon dioxide, kaolin, lactose, mannitol, maize starch, polyvinyl pyrrolidone, sorbitol, talcum and mixtures thereof. Examples of suitable humectant agents are selected from the group that contains glycerol, starch and mixtures thereof. Examples of suitable disintegration agents are selected from the group which contains for example alginic acid, amylose, calcium alginate, calcium carbonate, formaldehyde gelatine, sodium hydrogen carbonate, silicilic acid, sago starch, starch and mixtures thereof. Suitable lubricants are selected from the group which contains for example calcium or magnesium stearate, starch, stearinic acid, talcum and mixtures thereof.

Suitable pharmacologically tolerable binding agents that could constitute the coating or the inner layer of the coating, possibly in conjunction with the above-described auxiliary substances are, for example, compounds selected from the group containing hydroxypropylmethyl cellulose, polyethylene glycoles such as polyethylene glycol 1500, polyethylene glycol 2000, polyethylene glycol 3000, polyethylene glycol 4000, polyethylene glycol 6000, polyethylene glycol 8000, polyethylene glycol 10000, polyoxyethylene, polyoxyethylene-polyoxypropylene copolymers and mixtures thereof. This list is not exhaustive, indeed other binding agents known to a person skilled in the art can also be used. Suitable colorants are for example, food colorants, more particularly food colorant described in the German pharmaceutical colorant order. This list is not exhaustive, indeed other colorants known to a person skilled in the art can also be used.

The production of the coating of auxiliary substances and/or binding agents or the inner layer of the coating can be carried us by means of known methods, such as in a Wurster column or a sphere coater. For coating in a sphere coater the pellets, consisting exclusively of pancreatine, are introduced into the sphere coater and a previously produced homogeneous mixture of binding agents and auxiliary substances is sprayed in.

The gastric juices-resistant coating prevents the destruction of the pancreatine in the stomach as a result of the effect of the gastric acids on the acid-sensitive component of the pancreatine, more particularly the lipases. After passing through the stomach and the change in the pH value on entering the small intestine, the protective film forming the gastric juices resistant coating around the pancreatine core dissolves so that the pancreatine is released. The gastric-juice resistant material must be stable at a pH value of up to 5.5 and only permit the release of the pancreatine at a pH value of 5.5 and higher, preferably 6 and higher.

Suitable gastric juices-resistant materials which can be used for coating pellets are known from the state of the art. Normally such coatings contain a film-forming substances, at least a plasticiser and in some cases a separating agent. Suitable film-forming substances are for example selected from the group hydroxypropylmethyl cellulose acetate succinate (HPMCAS), hydroxypropylmethyl cellulose phthalate (HPMCP), cellulose acetate phthalate (CAP), polyvinylacetate phthalate (PVAP), methacrylic acid methylmethacrylate copolymerisates and methacrylic acid ethylacrylate copolymerisates as well as mixtures thereof. This list is not exhaustive, indeed other film-forming substances known to a person skilled in the art can also be used.

If, in addition to the film-forming substance, the gastric-juices resistant material contains a plasticiser, the proportion of the latter with regard to the film-forming substances should be between 1 and 20% by weight. Preferred plasticisers are monovalent alcohols with 12 to 30 carbon atoms, such as, for example, cetyl alcohol, stearyl alcohol, triethyl alcohol and mixtures thereof. This list is not exhaustive, indeed other plasticisers known to a person skilled in the art can also be used.

If in addition to the film-forming substances, and possibly also a plasticizer, the gastric juices-resistant material also contains a separating agent, the proportion of the latter should be between 0.5 and 5% by weight related to the film-forming substance. Examples of separating agents are castor oil and dimethicon. This list is not exhaustive, indeed other separating agents known to a person skilled in the art can also be used.

To produce the coating of gastric juices-resistant material, the film-forming substances, and if applicable the plasticiser and/or the separating agent can be dissolved or dispersed in a solvent in a known manner. After forming the coating, through drying for example, the solvent is removed. Suitable solvents are selected from the group which contains water, acetone, alcohols with 1 to 5 carbon atoms such as methanol, ethanol, n- and isopropanol, n- and tert-butanol or mixtures thereof.

The gastric juices-resistant coating can be produced by means of known methods, for example in a Wurster column or in a sphere coater. For coating in a sphere coater the pellets, which are already coated with a coating of auxiliary substances and binding agents, are introduced into the sphere coater and the gastric juices-resistant material is sprayed in.

The pancreatine pellets in accordance with the invention can be of a drop-like or spherical shape. Preferably the core is spherical, while the coating gives the pancreatine pellet its drop-like shape, which facilitates the administration of the pellets, for example from drop surfaces.

A drop-like shape offers the advantage that when falling the pellets orientate themselves in one direction. This allows simple counting out of the drop-like pancreatine pellets dispensed from the container, such as a drop surface.

The pancreatine pellets in accordance with the invention are particularly suitable for the treatment and/or prophylaxis of digestive disorders, acute pancreatitis, chronic pancreatitis, exocrine pancreas insufficiency, diabetes mellitus, more particularly type I and type II, and cystic fibrosis.

The pancreatine pellets in accordance with the invention can be used for the production of a pharmaceutical compound for the treatment of digestive disorders, acute pancreatitis, chronic pancreatitis, exocine pancreas insufficiency, diabetes mellitus and cystic fibrosis. Preferably the pharmaceutical composition contains the pancreatine pellets in accordance with the invention in a pharmacologically active dose which is suitable for oral administration.

The pancreatine pellets in accordance with the invention are also suitable for the production of nutritional substances or foodstuffs or as nutritional supplements.

The invention will be explained in more detail below with the aid of examples, which are not intended to limit the invention in any way, and with reference to the drawings.

The first form of embodiment of a pancreatine pellet 1 in accordance with the invention shown in FIG. 1 shows that this pellet exclusively consists of pancreatine 2. It has no coating.

In contrast to this, the second form of embodiment of a pancreatine pellet 1 in accordance with the invention has a core 2 and a single-layer coating 3. The core consists exclusively of pancreatine. The coating consists of auxiliary substances and binding agent. The coating 3 ensures the cohesion of the pancreatine core 2 and prevents, for example, mechanical or chemical destruction of the core 2.

Figure 3:
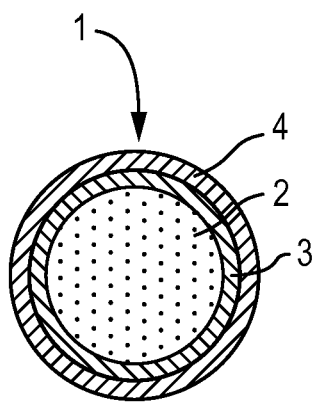
FIG. 3 shows a cross-section view of a third form of embodiment of a pancreatine pellet in accordance with the invention and a two-layer coating.

The third form of embodiment of the pancreatine pellet in accordance with the invention which is shown in FIG. 3 has a two-layer coating. The inner coating 3 surrounds the core 2 of pancreatine. In this way the pancreatine core is held together and is protected against mechanical or chemical destruction. The outer layer 4 consists of a material that is resistant to gastric juices.

Figure 4:
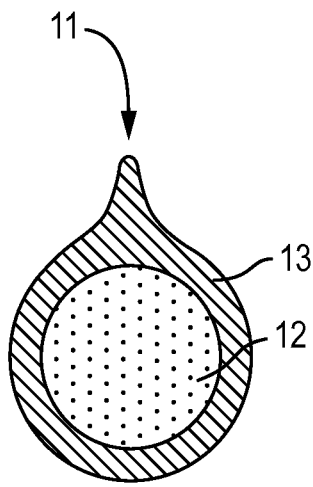
FIG. 4 shows a cross-section view of a fourth form of embodiment of a pancreatine pellet in accordance with the invention with a pancreatine core and a single-layer coating in a drop shape.
Figure 5:
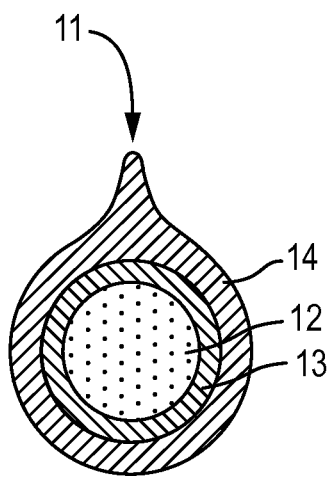
FIG. 5 shows a cross-section view of a fifth form of embodiment of a pancreatine pellet in accordance with the invention with a pancreatine core and a two-layer coating in a drop shape.

In FIGS. 4 and 5 the coating is in the shape of a drop. In the form of embodiment shown in FIG. 4, the pancreatine pellet 11 has a single-layer coating 13 in the shape of a drop which surrounds the spherical core 12 which consists exclusively of pancreatine. The coating 13 consists of auxiliary substances and binding agents. In FIG. 5 the coating is in two layers and comprises an inner layer 13 and an outer layer 14. Only the layer 15 has a drop-like shaped, whereas the inner layer 15 is spherical. The inner coating 13 consists of auxiliary substances and binding agents which hold the core together. The outer layer 14 consists of a material that is resistant to gastric juices.

LIST OF REFERENCE NUMBERS

1 Spherical pancreatine pellet
2 Pancreatine
3 Coating consisting of auxiliary substances and binding agents
4 Coating consisting of a material that is resistant to gastric juices
11 Drop-shaped pancreatine pellet
12 Pancreatine
13 Coating consisting of auxiliary substances and binding agents
14 Coating consisting of a material that is resistant to gastric juices

The invention claimed is:

1. A pancreatine pellet comprising a core consisting of pancreatine, and a coating comprising pancreatine,
   which coating has a first inner layer and a second outer layer,
   wherein the first inner layer surrounds the core and comprises auxiliary substances and binding agents, in an amount between 5-30% by weight of the pancreatine pellet,
   wherein the auxiliary substances, binding agents and pancreatine of the coating are homogeneously dispersed in the first inner layer,
   and wherein the second outer layer comprises a material that is resistant to gastric juices, in an amount between 10-30% by weight of the pancreatine pellet,
   and wherein the pancreatine pellet has a drop-like or spherical shape.

2. The pancreatine pellet according to claim 1, wherein the pellet is a micropellet.

3. The pancreatine pellet according to claim 1, wherein the pancreatine is obtained from the pancreas of a mammal.

4. The pancreatine pellet according to claim 1, wherein the diameter of the sphere or the shorter axis lies in the range of 0.4 to 0.8 mm.

5. A pharmaceutical composition, comprising a pharmacologically active quantity of pancreatine pellets which comprise a core consisting of pancreatine, which core contains no auxiliary substances and binding agents, and a coating comprising pancreatine,
   which coating has a first inner layer and a second outer layer,
   wherein the first inner layer surrounds the core and comprises auxiliary substances and binding agents, in an amount between 5-30% by weight of the pancreatine pellet,
   wherein the auxiliary substances, binding agents and pancreatine of the coating are homogeneously dispersed in the first inner layer,
   and wherein the second outer layer comprises a material that is resistant to gastric juices, in an amount between 10-30% by weight of the pancreatine pellet, and wherein the pancreatine pellet has a drop-like or spherical shape.

6. The pharmaceutical composition according to claim 5, in a dosage form that is suitable for oral administration.

* * * * *

UNITED STATES PATENT AND TRADEMARK OFFICE
CERTIFICATE OF CORRECTION

| | | |
|---|---|---|
| PATENT NO. | : 8,999,394 B2 | Page 1 of 1 |
| APPLICATION NO. | : 12/806942 | |
| DATED | : April 7, 2015 | |
| INVENTOR(S) | : Moest et al. | |

It is certified that error appears in the above-identified patent and that said Letters Patent is hereby corrected as shown below:

On the title page item [73] insert:

-- Nordmark Arzeimittel GmbH & Co., KG
Uetersen, Germany --

Signed and Sealed this
Fifteenth Day of September, 2015

Michelle K. Lee
*Director of the United States Patent and Trademark Office*